(12) United States Patent
Otsuki et al.

(10) Patent No.: US 11,130,864 B2
(45) Date of Patent: Sep. 28, 2021

(54) POLYMERIZABLE COMPOSITION AND KIT, AND POLYMERIZATION INITIATOR

(71) Applicant: Sun Medical Co., Ltd., Moriyama (JP)

(72) Inventors: Tamaki Otsuki, Moriyama (JP); Tatsuya Ori, Moriyama (JP); Yuya Yamamoto, Moriyama (JP); Takashi Yamamoto, Moriyama (JP); Masami Arata, Moriyama (JP)

(73) Assignee: SUN MEDICAL CO., LTD., Moriyama (JP)

( * ) Notice: Subject to any disclaimer, the term of this patent is extended or adjusted under 35 U.S.C. 154(b) by 56 days.

(21) Appl. No.: 16/076,393

(22) PCT Filed: Feb. 8, 2017

(86) PCT No.: PCT/JP2017/004587
§ 371 (c)(1),
(2) Date: Aug. 8, 2018

(87) PCT Pub. No.: WO2017/138567
PCT Pub. Date: Aug. 17, 2017

(65) Prior Publication Data
US 2019/0040261 A1 Feb. 7, 2019

(30) Foreign Application Priority Data

Feb. 9, 2016 (JP) .............................. JP2016-022576
Aug. 26, 2016 (JP) .............................. JP2016-165875

(51) Int. Cl.
| | | |
|---|---|---|
| *C08F 4/52* | (2006.01) | |
| *C09J 4/00* | (2006.01) | |
| *C08L 101/08* | (2006.01) | |
| *C09J 133/10* | (2006.01) | |
| *C09J 201/00* | (2006.01) | |
| *C08L 101/00* | (2006.01) | |
| *A61K 6/30* | (2020.01) | |
| *C08K 5/55* | (2006.01) | |
| *C08L 33/10* | (2006.01) | |
| *A61K 6/61* | (2020.01) | |
| *A61K 6/887* | (2020.01) | |

(52) U.S. Cl.
CPC .............. *C08L 101/08* (2013.01); *A61K 6/30* (2020.01); *C08F 4/52* (2013.01); *C08K 5/55* (2013.01); *C08L 33/10* (2013.01); *C08L 101/00* (2013.01); *C09J 4/00* (2013.01); *C09J 133/10* (2013.01); *C09J 201/00* (2013.01); *A61K 6/61* (2020.01); *A61K 6/887* (2020.01)

(58) Field of Classification Search
None
See application file for complete search history.

(56) References Cited

U.S. PATENT DOCUMENTS

| | | | |
|---|---|---|---|
| 4,095,017 A * | 6/1978 | Hsieh ..................... | B01J 31/143 526/186 |
| 5,041,508 A * | 8/1991 | Haruna ..................... | C09J 4/00 526/204 |
| 5,106,928 A | 4/1992 | Skoultchi et al. | |
| 5,143,884 A | 9/1992 | Skoultchi et al. | |
| 5,286,821 A | 2/1994 | Skoultchi | |
| 5,376,746 A | 12/1994 | Skoultchi | |
| 5,539,070 A | 7/1996 | Zharov et al. | |
| 5,616,796 A | 4/1997 | Pocius et al. | |
| 5,684,102 A | 11/1997 | Pocius et al. | |
| 5,690,780 A | 11/1997 | Zharov et al. | |
| 5,691,065 A | 11/1997 | Zharov et al. | |
| 5,718,977 A | 2/1998 | Pocius | |
| 5,795,657 A | 8/1998 | Pocius et al. | |
| 5,935,711 A | 8/1999 | Pocius et al. | |
| 6,248,846 B1 | 6/2001 | Zharov et al. | |
| 6,284,381 B1 | 9/2001 | Zharov et al. | |
| 2002/0018752 A1 * | 2/2002 | Krall ..................... | A61K 31/78 424/9.4 |
| 2003/0120005 A1 | 6/2003 | Webb et al. | |
| 2003/0228973 A1 | 12/2003 | Moren | |

(Continued)

FOREIGN PATENT DOCUMENTS

| | | | |
|---|---|---|---|
| JP | 2016-190805 A | 4/1988 | |
| JP | H07-72264 B2 | 8/1995 | |

(Continued)

OTHER PUBLICATIONS

Office Action dated Oct. 25, 2016, by the Japanese Patent Office in corresponding Japanese Patent Application No. 2016-165875 (2 pages).

(Continued)

*Primary Examiner* — Richard A Huhn
(74) *Attorney, Agent, or Firm* — Buchanan Ingersoll & Rooney PC

(57) ABSTRACT

The present invention improves the long-term storage stability of a polymerizable composition including an organoborane and a polymerizable monomer. A polymerizable composition includes (A) an organoborane, (B) an acidic group-free polymerizable monomer, and (C) a stabilizer for the organoborane (A), the composition being such that when the composition, after being allowed to stand at 45° C. for 48 hours, is analyzed with an E-type viscometer at a temperature of 25° C. and a rotational speed of 50 rpm, the ratio of the viscosity after the standing to the viscosity before the standing (viscosity after standing/viscosity before standing) is less than 100.

19 Claims, No Drawings

(56) References Cited

U.S. PATENT DOCUMENTS

| | | |
|---|---|---|
| 2004/0198935 A1 | 10/2004 | Webb et al. |
| 2005/0004332 A1* | 1/2005 | Jialanella ............... C08L 33/06 526/134 |
| 2005/0009946 A1 | 1/2005 | Oguri et al. |
| 2005/0107557 A1 | 5/2005 | Moren |
| 2006/0122319 A1* | 6/2006 | Kneafsey ............ C08F 290/148 524/556 |
| 2011/0294958 A1* | 12/2011 | Ahn ........................ C08F 4/52 525/267 |
| 2016/0002507 A1 | 1/2016 | Houlihan et al. |
| 2016/0108143 A1 | 4/2016 | Baran, Jr. et al. |

FOREIGN PATENT DOCUMENTS

| | | |
|---|---|---|
| JP | H07-116249 B2 | 12/1995 |
| JP | H11-60428 A | 3/1999 |
| JP | 2001-502689 A | 2/2001 |
| JP | 2003-96122 A | 4/2003 |
| JP | 3535167 B2 | 3/2004 |
| JP | 2005-514478 A | 5/2005 |
| JP | 4035634 B2 | 11/2007 |
| JP | 2008-502742 A | 1/2008 |
| JP | 2008-189581 A | 8/2008 |
| JP | 2008-308418 A | 12/2008 |
| JP | 2010-280891 A | 12/2010 |
| JP | 4975952 B2 | 4/2012 |
| JP | 2012-516932 A | 7/2012 |
| JP | 2013-194003 A | 9/2013 |
| JP | 2015-86162 A | 5/2015 |
| WO | 2012/160452 A1 | 11/2012 |
| WO | 2014/140138 A1 | 9/2014 |
| WO | 2014/209680 A2 | 12/2014 |

OTHER PUBLICATIONS

Sonnenschein et al.: "Physical and Chemical Probes of the Bond Strength between Trialkylboranes and Amines and Their Utility as Stabilized Free Radical Polymerization Catalysts," Macromolecules, vol. 39, No. 7, pp. 2507-2513, 2006 American Chemical Society.

* cited by examiner

POLYMERIZABLE COMPOSITION AND KIT, AND POLYMERIZATION INITIATOR

TECHNICAL FIELD

The present invention relates to a polymerizable composition which exhibits high adhesion to biological hard tissues and which has superior storage stability. More particularly, the present invention relates to a polymerizable composition containing an organoborane.

BACKGROUND ART

Patent Literature 1 and Patent Literature 2 disclose two-part initiator systems capable of initiating the polymerization of acrylic adhesive composition. The first part of the two-part system includes a stable organoborane-amine complex, and the second part includes an activator, for example, an organic acid such as (meth)acrylic acid or benzoic acid, or an aldehyde compound such as benzaldehyde. The activator liberates the amine from the complex, and allows the resultant organoborane to initiate radical polymerization.

Unfortunately, many organoborane-amine complexes are dissociated with time in (meth)acrylic monomer compositions, thus inducing the polymerization of the monomers. Because of this fact, the polymerization takes place earlier than designed. Further, the free amine exudes on a superficial portion of the cured polymer to adversely affect bonding durability or to cause a discoloration of the cured product.

Patent Literature 3 discloses an acrylic adhesive useful for polymer resins having low surface energy, the adhesive including at least one acrylic monomer, an organoborane-amine complex, and an effective amount of an acid for initiating the polymerization of the acrylic monomer.

Patent Literature 4 discloses an adhesive effective for polymer resins having low surface energy. This adhesive is an acrylic composition including an acrylic monomer, an organoborane-polyamine complex, and an amine-reactive compound.

Patent Literature 5 presents an initiator system including both an organoborane-amine complex and a β-ketone compound. In this initiator system, the β-ketone compound serves as a decomplexer and gradually frees the organoborane to provide a longer working time of the bonding composition.

However, similarly to Patent Literatures 1 and 2, Patent Literatures 3 to 5 are silent with respect to the stability of the organoborane-amine complex in the presence of a (meth) acrylic monomer, and do not describe any approaches to enhancing the storage stability. Further, Patent Literatures 1 to 5 do not report that their compositions exhibit excellent adhesion with respect to biological hard tissues (for example, tooth structures).

CITATION LIST

Patent Literature

Patent Literature 1: JP-B-H07-72264
Patent Literature 2: JP-B-H07-116249
Patent Literature 3: Japanese Patent No. 3535167
Patent Literature 4: Japanese Patent No. 4035634
Patent Literature 5: Japanese Patent No. 4975952

SUMMARY OF INVENTION

Technical Problem

An object of the present invention is to improve the long-term storage stability of a polymerizable composition including an organoborane and a polymerizable monomer.

Solution to Problem

The present inventors carried out extensive studies directed to achieving the above object. As a result, the present inventors have found that the object can be attained with polymerizable compositions having the following configurations, thus completing the present invention. For example, aspects of the present invention reside in the following [1] to [26].

[1] A polymerizable composition comprising (A) an organoborane, (B) an acidic group-free polymerizable monomer, and (C) a stabilizer for the organoborane (A), the composition being such that when the composition, after being allowed to stand at 45° C. for 48 hours, is analyzed with an E-type viscometer at a temperature of 25° C. and a rotational speed of 50 rpm, the ratio of the viscosity after the standing to the viscosity before the standing (viscosity after standing/viscosity before standing) is less than 100.

[2] The polymerizable composition described in [1], wherein the stabilizer (C) includes at least one selected from (C1) Lewis bases capable of forming a complex with the organoborane (A), and (C2) stabilizers other than (C1).

[3] The polymerizable composition described in [2], wherein the stabilizers (C) include (C1) a Lewis base capable of forming a complex with the organoborane (A), and (C2) a stabilizer other than (C1).

[4] The polymerizable composition described in [2] or [3], which comprises an organoborane-Lewis base complex formed from the organoborane (A) and the Lewis base (C1).

[5] The polymerizable composition described in any one of [2] to [4], wherein the stabilizer (C2) is at least one selected from (C2a) compounds which have a conjugated electron system, have a diketone structure, and have a hydrogen atom belonging to the conjugated electron system and not bonded directly to an aromatic ring, (C2b) compounds which have a conjugated electron system constituting at least part of a ring structure, and have a hydrogen atom belonging to the conjugated electron system and not bonded directly to an aromatic ring, (C2c) compounds which have a conjugated electron system containing five or more double bonds, and have a hydrogen atom belonging to the conjugated electron system and not bonded directly to an aromatic ring, and (C2d) at least one class of compounds selected from reducing compounds, hydrotalcite-like compounds and metal salts.

[6] The polymerizable composition described in [5], wherein the compound (C2a) is at least one selected from α-diketones and β-diketones.

[7] The polymerizable composition described in any one of [2] to [6], wherein the Lewis base (C1) is at least one selected from ammonia, amines, hydroxides and alkoxides.

[8] The polymerizable composition described in any one of [1] to [7], wherein the content of the stabilizer (C) is 0.001 to 100 parts by mass with respect to 100 parts by mass of the total of the components (A) and (B).

[9] The polymerizable composition described in any one of [1] to [8], wherein the organoborane (A) is a compound represented by BR$_3$ wherein R independently at each occurrence is a C$_{1-20}$ alkyl group.

[10] The polymerizable composition described in any one of [1] to [9], which further comprises a polymer (D) that is swollen by the polymerizable monomer (B) or is dissolved into the polymerizable monomer (B).

[11] The polymerizable composition described in [10], wherein the polymer (D) is a polymethyl (meth)acrylate.

[12] The polymerizable composition described in any one of [1] to [11], which further comprises a filler (E).

[13] The polymerizable composition described in [12], wherein the content of the filler (E) is 0.1 to 500 parts by mass with respect to 100 parts by mass of the total of the components (A) and (B).

[14] The polymerizable composition described in any one of [1] to [13], which is used in combination with an acid-containing pretreatment agent.

[15] A polymerizable composition kit comprising the polymerizable composition described in any one of [1] to [14], and an additive wherein the additive comprises an acidic group-containing compound (α) or a composition including the compound (α).

[16] The polymerizable composition kit described in [15], wherein the acidic group-containing compound (α) is an acidic group-containing polymerizable monomer.

[17] The polymerizable composition kit described in [16], wherein the acidic group-containing polymerizable monomer is at least one selected from 4-methacryloyloxyethyltrimellitic acid, 4-methacryloyloxyethyltrimellitic anhydride, and 10-methacryloyloxydecyl acid phosphate.

[18] A polymerizable composition kit comprising the polymerizable composition described in any one of [1] to [14], and an additive wherein the additive comprises a decomplexer (β) having reactivity with the Lewis base (C1) capable of forming a complex with the organoborane (A), or a composition including the decomplexer (β).

[19] The polymerizable composition kit described in [18], wherein the decomplexer (β) is an acid, an aldehyde, an isocyanate, an acid chloride, a sulfonyl chloride, or a mixture of two or more of these compounds.

[20] The polymerizable composition described in any one of [1] to [14], or the polymerizable composition kit described in any one of [15] to [19], which is used as an adhesive.

[21] The polymerizable composition described in any one of [1] to [14], or the polymerizable composition kit described in any one of [15] to [19], which is used in a medical and/or a dental application.

[22] The polymerizable composition or the polymerizable composition kit described in [21], which is used as an adhesive in a medical and/or a dental application in combination with a tooth surface-treating agent including an acid or an oxidizer.

[23] A polymerization initiator comprising (A) an organoborane, and (C2) a stabilizer other than Lewis bases capable of forming a complex with the organoborane (A).

[24] The polymerization initiator described in [23], which further comprises (C1) a Lewis base capable of forming a complex with the organoborane (A).

[25] The polymerization initiator described in [24], which comprises an organoborane-Lewis base complex formed from the organoborane (A) and the Lewis base (C1).

[26] The polymerization initiator described in any one of [23] to [25], which further comprises a polymerization inhibitor.

Advantageous Effects of Invention

The polymerizable compositions provided according to the present invention include an organoborane and a polymerizable monomer, and attain superior storage stability over a long term. The compositions have high adhesion with respect to biological hard tissues, and are therefore highly useful particularly as medical and/or dental materials.

DESCRIPTION OF EMBODIMENTS

Embodiments of the present invention will be described below.

[Polymerizable Compositions]

A polymerizable composition of the present invention includes an organoborane (A), an acidic group-free polymerizable monomer (B), and a stabilizer (C) for the organoborane (A). These components will be also referred to as the component (A), the component (B) and the component (C), respectively. For example, the components (A) to (C) exist in a single system (e.g., a container). The polymerizable composition is, for example, a mixture including the components (A) to (C). In an embodiment of the polymerizable composition of the invention, the components (A) to (C) are stored in a single container.

The organoborane (A) acts as a polymerization initiator for the monomer (B). The stabilizer (C) suppresses the activity of the organoborane (A) and effectively reduces the action of the component (A) as a polymerization initiator, thus enhancing the long-term storage stability of the polymerizable composition containing the components (A) to (C).

The polymerizable composition of the invention is preferably used in combination with a pretreatment agent containing an acid such as a Lewis acid. According to this embodiment, the acid acts so as to release the component (A) from stabilization by the component (C) and consequently the component (A) is, for example, liberated and immediately initiates the polymerization reaction of the component (B).

(Organoboranes (A))

Examples of the organoboranes (A) include organoboranes (A1) in which the boron atom has an empty p orbital or electrophilic properties, and organoboranes (A2) in which the boron atom is a tetravalent anion.

A preferred organoborane (A1) is a compound represented by BR$_3$. In the formula, B is a boron atom and R independently at each occurrence is a C$_{1-20}$ alkyl group, a C$_{6-20}$ aryl group, a C$_{3-20}$ saturated or unsaturated alicyclic group, a C$_{1-20}$ alkoxy group, or a C$_{2-20}$ alkyl(amino)alkoxy group (N(R$^1$)$_m$(H)$_n$—R$^2$O— wherein R$^1$ is an alkyl group, R$^2$ is an alkylene group, m is 1 or 2, and n is 1 or 0). Two or more of the groups R may be linked to one another to form a ring such as an aliphatic ring. From the point of view of activity, however, it is preferable that no such rings be formed. The groups R are preferably any of the above-described groups other than the aryl groups, more preferably the alkyl groups, still more preferably C$_{1-10}$ alkyl groups, and particularly preferably C$_{1-5}$ alkyl groups. It is preferable that all the groups R be the same.

Examples of the compounds represented by BR$_3$ include trialkylboranes such as trimethylborane, triethylborane, tripropylboranes including tri-n-propylborane and triisopropylborane, and tributylboranes including tri-n-butylborane, triisobutylborane and tri-sec-butylborane; alkyl and alicyclic ring-containing boranes such as ethyldicyclohexylborane and (1,3-cyclopentadienyl)dimethylborane; and aryldialkylboranes such as phenyldiethylborane. These compounds may be substituted with an alkoxy group or an alkyl(amino) alkoxy group in place of at least one substituent on the boron atom. For example, $H_3C-NH-(CH_2)_2-O-B(CH_2CH_3)_2$, and $H_3C-NH-(CH_2)_2-O-B(C_6H_{11})_2$ may be mentioned. When, as is the case in the above example compounds, the compound has an alkyl(amino)alkoxy group and is capable of forming an intramolecular coordination bond to the boron atom, the stabilizer may be the stabilizer (C2) alone without the Lewis base (C1) described later.

In the organoborane (A1), it is preferable that one or more carbon atoms be bonded directly to the boron atom. If, however, a π-electron group such as an aromatic ring is bonded to an empty p-orbital of the boron atom in a way that they can form a conjugated system, as is the case for triphenylborane, the compound is so stabilized that its activity is decreased at times.

The organoborane (A2) is preferably a compound represented by $M^4BR_4^-$. In the formula, M is an alkali metal, B is a boron atom, and R independently at each occurrence is a hydrogen atom, a $C_{1-20}$ alkyl group, a $C_{6-20}$ aryl group, a $C_{3-20}$ saturated or unsaturated alicyclic group, a $C_{1-20}$ alkoxy group, or a $C_{2-20}$ alkyl (amino)alkoxy group. Two or more of the groups R may be linked to one another to form a ring such as an aliphatic ring. Examples of the compounds represented by $M^+BR_4^-$ include $Li^+[HB(CH(CH_3)CH_2CH_3)_3]^-$. In the organoborane (A2), it is preferable that one or more hydrogen atoms be bonded directly to the boron atom. When the organoborane is a compound represented by $M+BR_4^-$, the stabilizer may be the stabilizer (C2) alone without the Lewis base (C1) described later.

The organoboranes (A) may be used singly, or two or more may be used in combination.

The polymerizable composition of the present invention usually contains the organoborane (A) in the range of 0.001 to 50 parts by mass, preferably 0.01 to 30 parts by mass, and more preferably 0.1 to 10 parts by mass with respect to 100 parts by mass of the total of the organoborane (A) and the polymerizable monomer (B). This embodiment is advantageous in terms of polymerization efficiency. When the organoborane (A) is in the form of a complex with the stabilizer (C), in particular, with the Lewis base (C1), the content of the organoborane (A) includes the amount of the organoborane constituting the complex.

<Acidic Group-Free Polymerizable Monomers (B)>

The polymerizable monomer (B) has at least one ethylenically unsaturated group capable of undergoing radical polymerization and is free from acidic groups. Examples of the acidic groups include carboxylic acid groups such as carboxyl groups and carboxylic anhydride groups, phosphoric acid groups, thiophosphoric acid groups, pyrophosphoric acid groups, sulfonic acid groups and phosphonic acid groups.

A preferred monomer (B) is a (meth)acrylic monomer. The term "(meth)acrylic monomer" is a collective term for both acrylic monomer and methacrylic monomer.

Examples of the (meth)acrylic monomers include (meth) acrylate esters of monohydric alcohols (in particular, $C_{1-12}$ alkanols) such as methyl (meth)acrylate, ethyl (meth)acrylate, propyl (meth)acrylate, butyl (meth)acrylate, ethylhexyl (meth)acrylate and tetrahydrofurfuryl (meth)acrylate; mono (meth)acrylate esters and di(meth)acrylate esters of polyhydric alcohols such as ethylene glycol, diethylene glycol, triethylene glycol, tetraethylene glycol, polyethylene glycol, propylene glycol, dipropylene glycol, tripropylene glycol, tetrapropylene glycol, pentapropylene glycol, glycerol and trimethylolpropane; di(meth)acrylate esters of ethoxylated diphenolpropane and propoxylated diphenolpropane; and (meth)acrylamide compounds such as N,N-dimethyl (meth)acrylamide, N,N-diethyl (meth)acrylamide, N-butyl (meth)acrylamide, N-((meth)acryloyl)morpholine, N-((meth)acryloyl)piperidine and 2-hydroxyethyl (meth)acrylamide. Of these, (meth)acrylate esters of monohydric alcohols are preferable from the point of view of the storage stability of the polymerizable composition.

The polymerizable monomers (B) may be used singly, or two or more may be used in combination.

<Stabilizers (C) for Organoboranes (A)>

The stabilizer (C) serves to hold down the high reactivity of the organoborane (A) to an appropriate level. Because the organoborane (A) in the polymerizable composition is rendered less reactive by the stabilizer (C), the polymerizable composition exhibits sufficient storage stability without undergoing polymerization and curing even when the organoborane (A) and the acidic group-free polymerizable monomer (B) coexist under, for example, room temperature conditions. The component (A) is released from stabilization by the component (C) upon addition of an acidic group-containing compound or a decomplexer to the polymerizable composition, and consequently the component (A) is, for example, liberated and immediately initiates the polymerization reaction of the component (B).

The stabilizer (C) may be at least one selected from Lewis bases (C1) capable of forming a complex with the organoborane (A), and stabilizers (C2) other than (C1).

<Lewis Bases (C1)>

The polymerizable composition of the present invention preferably contains at least a Lewis base (C1) as the stabilizer (C). In the preparation of the composition, the organoborane (A) and the Lewis base (C1) may be added to the system separately. Alternatively, an organoborane-Lewis base complex may be formed beforehand and the complex may be added to the system.

The organoborane-Lewis base complex may be prepared by a known method. Usually, the Lewis base (C1) is reacted with the organoborane (A) in an atmosphere of an inert gas such as nitrogen while slowly stirring the reaction system. Preferably, the organoborane (A) is dropped to the reaction system, and cooling is performed if the reaction generates heat. When the vapor pressure of the compounds is high, the reaction temperature is preferably set to not more than 80° C., and more preferably not more than 70° C. The complex that is prepared is preferably stored in a closed container in a cool dark place.

The molar ratio (C1/A) of the Lewis base (C1) to the organoborane (A) in the complex is preferably 0.5 to 3.0, and more preferably 1.0 to 2.0. This embodiment is advantageous in terms of the stability of the complex, and the adhesion of the polymerizable composition used as an adhesive.

Examples of the solvents used in the production of the complex include ethers such as tetrahydrofuran and diethyl ether; and low-molecular weight alkanes such as hexane and heptane. After the completion of the reaction, the solvent is removed by, for example, using a rotary evaporator.

The content of the organoborane-Lewis base complex in the polymerizable composition of the present invention is such that the polymerization of the polymerizable monomer takes place easily upon addition of an acidic group-containing compound or a decomplexer to the composition and is also such that the composition attains outstanding adhesion to biological hard tissues (e.g., bones, teeth).

Examples of the Lewis bases (C1) include ammonia, amines, hydroxides and alkoxides, with amines being preferable. Examples of the amines include primary to tertiary monoamines, polyamines (with the proviso that heterocyclic amines and amines having an amidine structure are excluded from these monoamines and polyamines), heterocyclic amines (with the proviso that amines having an amidine structure are excluded), and amines having an amidine structure. Examples further include conjugated imines and primary amines having a hydrogen bond accepting group described in JP-A-2003-517009. Of these, monoamines and polyamines are preferable.

As is the case in amides (R—CO—NH$_2$) and carbamides (R—NH—CO—NH$_2$), the Lewis basicity may be decreased if a strong electron-withdrawing atom (group) such as carbonyl group is present near the Lewis base moiety.

<<Primary to Tertiary Monoamines>>

Examples of the substituents for hydrogen atoms in the monoamines include organic groups, with $C_{1-10}$ alkyl groups, aryl groups, arylalkyl groups, alkoxy groups, alkoxyalkyl groups, hydroxyalkyl groups, carboxyalkyl groups and polyoxyalkyl groups being preferable. The aryl groups may be substituted with at least one selected from alkyl groups, alkoxy groups, carboxyl groups, alkoxycarbonyl groups, aldehyde groups and halogen atoms, in place of one or more hydrogen atoms.

Specific examples include primary monoamines such as ethylamine, butylamine, hexylamine, octylamine, benzylamine, methoxyethylamine, methoxypropylamine, methoxybutylamine, ethoxypropylamine, propoxypropylamine, ethanolamine and polyoxyalkylenemonoamine; secondary monoamines such as dimethylamine, diethylamine, dibutylamine, diethanolamine, N-phenylglycine and N-tolylglycine; and tertiary amines such as triethylamine, methyldiethanolamine, dimethylethanolamine, triethanolamine, N,N-dimethylaniline, N,N-dimethyl-p-tert-butylaniline, N,N-dimethyl-p-chloroaniline, N,N-dimethylanisidine, N,N-dimethylaminobenzoic acid and alkyl esters thereof, N,N-diethylaminobenzoic acid and alkyl esters thereof, N,N-dimethylaminobenzaldehyde, N,N-dimethyl-p-toluidine, N,N-diethyl-p-toluidine, and N,N-diethanol-p-toluidine. Of these, primary monoamines are preferable.

<<Polyamines>>

Examples of the polyamines include diamines, triamines and tetramines.

Examples of the diamines include aliphatic diamines such as 1,2-diaminoethane, 1,3-diaminopropane, 1,5-diaminopentane, 1,6-diaminohexane, 1,12-diaminododecane, 2-methyl-1,5-diaminopentane, 3-methyl-1,5-diaminopentane, dimethylaminopropylamine, dimethylaminoethylamine and dimethylaminobutylamine; and alicyclic diamines such as isophoronediamine. The diamines preferably have at least two carbon atoms, more preferably at least three carbon atoms, between the two amino groups.

Examples of the triamines include aliphatic triamines such as diethylenetriamine and dipropylenetriamine. Examples of the tetramines include aliphatic tetramines such as triethylenetetramine. The triamines and tetramines preferably have at least two carbon atoms between amino groups.

Examples of the polyamines further include polyoxyalkylenepolyamines having a molecular weight of not more than 1000. Examples of the polyoxyalkylenepolyamines include polyethylene oxide diamine, polypropylene oxide diamine, polypropylene oxide triamine, diethylene glycol dipropyl amine, triethylene glycol dipropyl amine, polytetramethylene oxide diamine, poly(ethylene oxide-iso-propylene oxide) diamine, poly(ethylene oxide-iso-propylene oxide) triamine, and trimethylolpropane tris(poly(propylene glycol), amine terminated) ether.

<<Heterocyclic Amines>>

The heterocyclic amine is an aliphatic heterocyclic compound or aromatic heterocyclic compound having at least one nitrogen atom in the heterocycle, and may further have one or more oxygen atoms, sulfur atoms or double bonds in the heterocycle. The heterocyclic amine may be a polycyclic compound having a nitrogen atom in at least one of the rings. The heterocyclic amine is preferably a compound represented by the formula (1):

[Chem. 1]

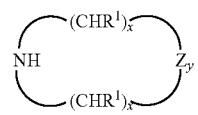

In the formula (1), $R^1$ independently at each occurrence is a hydrogen atom, a $C_{1-10}$ alkyl group or a $C_{3-10}$ cycloalkyl group, and preferably a hydrogen atom or a methyl group. Z independently at each occurrence is an oxygen atom, a sulfur atom or —N($R^2$)—, and preferably —N($R^2$)—. $R^2$ independently at each occurrence is a hydrogen atom, a $C_{1-10}$ alkyl group, a $C_{3-10}$ cycloalkyl group, a $C_{6-10}$ aryl group or a $C_{7-10}$ aralkyl group, preferably a hydrogen atom or a $C_{1-4}$ alkyl group, and more preferably a hydrogen atom or a methyl group. The letter x independently at each occurrence is an integer of 1 to 9 with the proviso that the total of all x is 2 to 10. Preferably, x is an integer of 1 to 4, and the total of all x is 3 to 5. The letter y independently at each occurrence is 0 or 1. The hydrogen atom in —NH— in the formula may be substituted by an amino group or an aminoalkyl group, and the alkylene groups constituting the ring structure may be partly substituted by an alkenylene group.

Examples of the heterocyclic amines include such compounds represented by the above formula (1) as aziridine, pyrrolidine, 3-pyrroline, piperidine, morpholine, N-(3-aminopropyl)morpholine, piperazine, 1-amino-4-methylpiperazine, homopiperazine and thiazolidine, and 1,3,3-trimethyl-6-azabicyclo[3.2.1]octane, 1,4-diazabicyclo[2.2.2]octane and 4-(N,N-dimethylamino)-pyridine.

<<Amines Having Amidine Structure>>

The amine having an amidine structure is preferably a compound represented by the formula (2):

[Chem. 2]

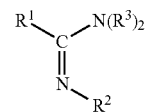

In the formula (2), $R^1$ to $R^3$ are, each independently at each occurrence, a hydrogen atom, a $C_{1-10}$ alkyl group or a $C_{3-13}$ cycloalkyl group, and preferably a hydrogen atom, a $C_{1-4}$ alkyl group or a $C_{5-6}$ cycloalkyl group. $R^1$ may be —N($R^3$)$_2$. Two or more of $R^1$ to $R^3$ may be linked to one another to form a ring structure such as a monocyclic or bicyclic structure, and such a ring may have one or more nitrogen atoms, oxygen atoms, sulfur atoms or double bonds. Specifically, $R^2$ and one $R^3$ may be bonded to form a monocyclic structure, or $R^1$ and one $R^3$, and $R^2$ and the other $R^3$ may be bonded to form a bicyclic structure.

Examples of the amines having an amidine structure include 1,8-diazabicyclo[5.4.0]undec-7-ene, 1,5-diazabicyclo[4.3.0]non-5-ene, 2-methyl-2-imidazoline, 2-methylimidazole, tetrahydropyrimidine and 1,1,3,3-tetramethylguanidine.

<<Hydroxides and Alkoxides>>

The Lewis base (C1) may be a hydroxide and/or an alkoxide, each represented by $(R—O^-)_m M^{n+}$. In the formula, R independently at each occurrence is a hydrogen atom or an alkyl group. The letter m is an integer. $M^{n+}$ is a counter ion and is, for example, sodium, potassium, tetraalkylammonium, or a combination thereof. The letter n is an integer.

<Stabilizers (C2)>

From the point of view of long-term storage stability, the polymerizable composition of the present invention preferably further contains a stabilizer (C2) other than the stabilizers (C1) described above. The stabilizer (C2) is preferably a component having a radical scavenging function, and is, for example, a compound which has a conjugated electron system and has a hydrogen atom belonging to the conjugated electron system and not bonded directly to an aromatic ring. In the present specification, the phrase "hydrogen atom belonging to the conjugated electron system and not bonded directly to an aromatic ring" refers to a hydrogen atom which is bonded to a carbon atom or the like constituting the structural skeleton of the conjugated electron system, or a hydrogen atom which is bonded to a carbon or oxygen atom bonded to a carbon atom or the like constituting the structural skeleton of the conjugated electron system.

Even when the hydrogen atom belongs to the conjugated electron system, the advantageous effects of the present invention are hardly obtained if the hydrogen atom is bonded directly to an aromatic ring. In the case of, for example, benzil (other name: diphenylethanedione), little effects are obtained for the stabilization of the organoborane (A). As long as there is a hydrogen atom that belongs to the conjugated electron system and is not bonded directly to an aromatic ring, no problems are encountered even if an aromatic ring is simply present or if an aromatic ring constitutes the conjugated electron system. For example, 1-phenyl-1,2-propanediol can realize high stability of the organoborane (A).

Examples of the stabilizers (C2) include stabilizers (C2a) to (C2d) below. The stabilizers (C2) may be used singly, or two or more may be used in combination.

<<Stabilizers (C2a)>>

The stabilizer (C2a) is a compound which has a conjugated electron system, has a diketone structure, and has a "hydrogen atom belonging to the conjugated electron system and not bonded directly to an aromatic ring". Examples of the stabilizers (C2a) include α-diketones, β-diketones and γ-diketones. From the point of view of the storage stability of the polymerizable composition, α-diketones and β-diketones are preferable, and α-diketones are more preferable. The compounds having a diketone structure include those compounds which can establish a conjugated electron system by keto-enol tautomerism.

Examples of the stabilizers (C2a) include compounds represented by the following formula:

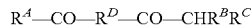

In the formula, $R^A$ is a hydrocarbon group, an ether bond-containing group or a transition metal, preferably a hydrocarbon group, more preferably a $C_{1-20}$ alkyl group or a $C_{6-30}$ aryl group, and particularly preferably a methyl group, an ethyl group, a propyl group or a phenyl group. $R^B$ and $R^C$ are each independently a hydrogen atom, a hydrocarbon group, an ether bond-containing group or a transition metal, preferably a hydrogen atom or a hydrocarbon group, and more preferably a hydrogen atom. $R^D$ is a direct bond, a methylene group or a 1,2-ethylene group. The hydrogen atoms bonded to the α-carbon atoms in the diketone realize marked effects of the present invention.

Examples of the stabilizers (C2a) include α-diketones such as 1-phenyl-1,2-propanedione and 2,3-butanedione; β-diketones such as acetylacetone; and γ-diketones such as 2,5-hexanedione.

<<Stabilizers (C2b)>>

The stabilizer (C2b) is a compound which has a conjugated electron system constituting at least part of a ring structure, and has a "hydrogen atom belonging to the conjugated electron system and not bonded directly to an aromatic ring" (with the proviso that the stabilizers (C2a) described above and stabilizers (C2c) described below are excluded). The stabilizer (C2b) may have or may not have an aromatic ring. The reason why the stabilizer (C2b) may not have an aromatic ring is that the planar structure of the conjugated electron system is maintained with ease due to the stereocontrol by the ring structure. Examples of the stabilizers (C2b) include ascorbic acid, calciferol, α-tocopherol, and polyphenols (compounds having a plurality of phenolic hydroxyl groups (e.g., hydroxyl groups bonded to aromatic rings such as benzene rings and naphthalene rings) in the molecule), for example, flavonoids including flavonols such as quercetin. From the point of view of the storage stability of the polymerizable composition, the stabilizers (C2b) other than polyphenols are preferable.

In the present specification, unless otherwise mentioned, those of the example compounds which have optical isomers may be any of such optical isomers. For example, ascorbic acid, which has optically isomeric forms, may be any of the optical isomers.

<<Stabilizers (C2c)>>

The stabilizer (C2c) is a compound which has a conjugated electron system containing five or more double bonds, and has a "hydrogen atom belonging to the conjugated electron system and not bonded directly to an aromatic ring" (with the proviso that the stabilizers (C2a) described above are excluded), and is preferably a hydrocarbon compound satisfying these requirements. The double bonds are preferably carbon-carbon double bonds. The number of double bonds does not count the number of double bonds which are written in an aromatic ring in the formula. It is considered that the energy barrier is lowered and the transfer of hydrogen and radicals is facilitated with increasing number of conjugated electrons. It is therefore preferable that the number of double bonds be 7 or more. The upper limit of the number of double bonds is, for example, 20. For example, the stabilizer (C2) is a nonaromatic compound which may contain an aliphatic ring, with specific examples including carotenes such as α-carotene and β-carotene.

<<Stabilizers (C2d)>>

The stabilizer (C2d) is at least one compound selected from reducing compounds, hydrotalcite-like compounds and metal salts, other than the stabilizers (C2a) to (C2c).

Examples of the reducing compounds include vitamins, and organic sulfinate salts, inorganic sulfur compounds and organotin compounds having a reducing action based on heteroatoms such as sulfur atoms and tin atoms.

Examples of the vitamins include water-soluble B vitamins.

Examples of the organic sulfinate salts include salts of aromatic sulfinic acids such as benzenesulfinic acid, o-toluenesulfinic acid, p-toluenesulfinic acid, ethylbenzenesulfinic acid, decylbenzenesulfinic acid, dodecylbenzenesulfinic acid, chlorobenzenesulfinic acid and naphthalenesulfinic acid.

Examples of the inorganic sulfur compounds include salts of such compounds as sulfurous acid, bisulfurous acid, metasulfurous acid, metabisulfurous acid, pyrosulfurous acid, thiosulfuric acid, 1-thionous-2-thionic acid, 1,2-thionic acid, hyposulfurous acid and hydrosulfurous acid.

Examples of the organotin compounds include tin compounds substituted with one to four organic groups. Examples of the monosubstituted organotin compounds include methyltin, butyltin, octyltin, and monoester tin compounds. Examples of the disubstituted organotin compounds include dibutyltin oxide and dibutyltin chloride. Examples of the trisubstituted organotin compounds include tributyltin. Examples of the tetrasubstituted organotin compounds include tetrabutyltin, dibutyltin maleate and dibutyltin dilaurate. Of these, in particular, dibutyltin dilaurate is preferably used. Examples of the organic groups include $C_{1-20}$ alkyl groups, fatty acid residues such as lauric acid residue, and dicarboxylic acid residues such as maleic acid residue.

For example, the organotin compounds may be compounds represented by the following formula wherein R is an alkyl group such as a methyl group, a butyl group or an octyl group, and preferably a $C_{1-20}$ alkyl group, X is a fatty acid residue such as lauric acid residue ($C_{11}H_{23}$—COO—), and n is an integer, for example, an integer of 0 to 20.

[Chem. 3]

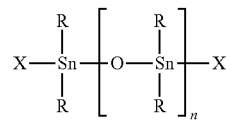

Examples of the hydrotalcite-like compounds include double hydroxides represented by the general formula $M^1_{8-x}M^2_x(OH)_{16}CO_2 \cdot nH_2O$. $M^1$ is $Mg^{2+}$, $Fe^{2+}$, $Zn^{2+}$, $Ca^{2+}$, $Li^{2+}$, $Ni^{2+}$, $Co^{2+}$ or $Cu^{2+}$, $M^2$ is $Al^{3+}$, $Fe^{3+}$ or $Mn^{3+}$, x is an integer of 1 to 7, and n is an integer. Examples of the hydrotalcite-like compounds further include magnesium aluminometasilicate $Al_2O_3 \cdot MgO \cdot 1.7SiO_2 \cdot nH_2O$.

Examples of the metal salts include transition metal salts having reducing properties. Ferric chloride ($FeCl_3$) is preferably used.

<Content of Stabilizer (C)>

The polymerizable composition of the present invention usually contains the component (C) in the range of 0.001 to 100 parts by mass, preferably 0.005 to 30 parts by mass, and more preferably 0.01 to 20 parts by mass with respect to 100 parts by mass of the total of the components (A) and (B). The lower limit of the above range advantageously ensures that the polymerizable composition will exhibit superior stability. The upper limit of the above range advantageously ensures that polymerization will be initiated immediately after an acidic group-containing compound or a decomplexer is added to the polymerizable composition.

In the polymerizable composition of the present invention, the molar ratio (A/C2) of the organoborane (A) to the stabilizer (C2) is preferably 0.1 to 20, more preferably 0.5 to 10, and still more preferably 1 to 5. The upper limit of the above range advantageously ensures that the organoborane (A) is stabilized. The lower limit is advantageous in that the polymerization of the polymerizable composition can be initiated immediately.

In the polymerizable composition of the present invention, the molar ratio (C1/C2) of the Lewis base (C1) to the stabilizer (C2) is preferably 0.1 to 20, more preferably 0.5 to 10, and still more preferably 1 to 5. The upper limit of the above range advantageously ensures that the composition will be prevented from polymerization during storage. The lower limit is advantageous in terms of the initiation of the polymerization of the composition.

<Polymers (D)>

The polymer (D) is a component that is swollen by the polymerizable monomer or is dissolved into the polymerizable monomer. The use of the polymer (D) increases the viscosity of the liquid including the polymerizable monomer, and also allows the curing time to be controlled.

The weight average molecular weight of the polymer (D) relative to polymethyl methacrylate is preferably 1,000 to 2,000,000, and more preferably 10,000 to 800,000. The molecular weight is measured by gel permeation chromatography.

The (volumetric) average particle size of the polymer (D) is preferably 0.1 to 300 μm, more preferably 10 to 100 μm, and still more preferably 10 to 50 μm. For example, the polymer (D) is a powder. The average particle size is measured with a grain size distribution analyzer (laser diffraction/scattering method).

For example, the polymers (D) may be homopolymers and/or copolymers of monofunctional polymerizable monomers (e.g., monofunctional (meth)acrylic monomers) which can be used as the polymerizable monomers (B). Specific examples include polymethyl (meth)acrylate, polyethyl (meth)acrylate, polypropyl (meth)acrylate, polybutyl (meth)acrylate, and copolymers of methyl (meth)acrylate and ethyl (meth)acrylate, with polymethyl (meth)acrylate being preferable.

The polymers (D) may be used singly, or two or more may be used in combination.

When the polymer (D) is used, the content of (D) in the polymerizable composition of the invention, although variable depending on use applications, is, for example, 1 to 300 parts by mass with respect to 100 parts by mass of the total of the components (A) and (B).

<Fillers (E)>

The polymerizable composition of the present invention may include a filler (E) as required. The use of the filler (E) allows the viscosity of the polymerizable composition to be controlled, and the polymerization rate or the curing time to be controlled to a desired level.

Examples of the fillers (E) include inorganic fillers, organic fillers, and organic composite fillers combining organic components and inorganic components.

Examples of the inorganic fillers include amorphous silica, alumina, quartz, alumina quartz, silica-alumina compounds, silica-zirconia compounds, silica-titania compounds, titanium oxide, glass (including barium glass), zirconium oxide, calcium carbonate, kaolin, clay, mica, aluminum sulfate, barium sulfate, calcium sulfate, calcium phosphate and hydroxyapatite. The inorganic fillers may be surface treated beforehand with agents such as silane-coupling agents or titanate-coupling agents.

The organic fillers may be polymers which are not substantially dissolved into the polymerizable monomers. Examples thereof include fillers including such polymers as polyethylene, polypropylene, ethylene propylene copolymer, ethylene propylene terpolymer, polyisoprene, ethylene vinyl acetate copolymer, silicone polymer and acrylate ester copolymer.

Examples of the organic composite fillers include those fillers which are obtained by polymerizing a polymerizable monomer so as to coat the surface of the aforementioned inorganic filler followed by crushing. Specific examples include fillers (TMPT.f) obtained by polymerizing polymerizable monomers based on trimethylolpropane tri(meth)acrylate (TMPT) so as to coat fine powdery silica, and crushing the resultant polymer.

The (volumetric) average particle size of the filler (E) is preferably 0.01 to 100 μm. More preferably, fillers (E) having different particle sizes are used as a mixture. The average particle size is measured with a grain size distribution analyzer (laser diffraction/scattering method).

When the filler (E) is used, the content of (E) in the polymerizable composition of the invention, although variable depending on use applications, is, for example, 0.1 to 500 parts by mass with respect to 100 parts by mass of the total of the components (A) and (B).

<Additional Components (F)>

In addition to the components described hereinabove, the polymerizable composition of the present invention may contain additional components (F). Examples of the additional components (F) include polymerization inhibitors (used in small amounts which ensure that the decomposition of the polymerizable monomer during storage will be prevented or reduced and which do not substantially cause a decrease in the polymerization rate of the polymerizable composition, typically in amounts of 10 to 10,000 ppm based on the mass of the polymerizable monomer), peroxides (typically used in amounts of not more than 2 mass % based on the mass of the whole composition), and photopolymerization initiators (typically used in amounts of not more than 5 mass-% based on the mass of the whole composition).

A solvent may be added to the polymerizable composition of the invention as required. Examples of the solvents include water; and organic solvents such as alcohols including ethanol and propanol, and ketones including acetone. The water may be, for example, distilled water, ion-exchanged water, or purified water (the Japanese Pharmacopoeia). Instead of water, use may be made of physiological saline or the like. Purified water (the Japanese Pharmacopoeia) is particularly preferable. The solvents may be used singly, or two or more may be used in combination.

<Preparation of Polymerizable Compositions>

The polymerizable composition of the present invention may be prepared by mixing the aforementioned components (A) to (C) optionally together with other components. When the component (C) that is used includes at least the Lewis base (C1), the composition may be prepared in such a manner that the base is allowed to form an organoborane-Lewis base complex beforehand, and the complex is mixed with the component (B) and optionally with the component (C2) and other components.

In the polymerizable composition of the present invention, the total amount of the components (A) to (C) is preferably not less than 5 mass %, more preferably not less than 10 mass %, and still more preferably not less than 20 mass %. The upper limit of the total amount of the components (A) to (C) may be 100 mass % or may be determined appropriately in accordance with the amounts of other components which are added to the polymerizable composition.

The polymerizable composition of the present invention remains as such stably unless a polymerization initiating component such as an acidic group-containing compound or a decomplexer is added thereto. For example, in an embodiment, the polymerizable composition of the invention is not cured even when it is allowed to stand at 45° C. for 48 hours, and is preferably not cured even when it is allowed to stand at 45° C. for 96 hours, and particularly preferably for 168 hours. In an embodiment, the polymerizable composition of the invention is not cured even when it is allowed to stand at 25° C. for 3 to 12 months. The degree of curing may be determined by, for example, visually checking whether the composition has fluidity like liquid (i.e., has not been cured) or not (i.e., has been cured).

In an embodiment, the polymerizable composition of the present invention is such that when the composition is allowed to stand at 45° C. for 48 hours, the ratio of the viscosity after the standing to the viscosity before the standing (viscosity after standing/viscosity before standing (initial viscosity)) is less than 100, preferably less than 70, more preferably less than 50, still more preferably 1 to 30, and particularly preferably 1 to 5. Further, when the polymerizable composition is allowed to stand at 45° C. preferably for 96 hours or particularly preferably for 168 hours, the viscosity ratio (viscosity after standing/viscosity before standing (initial viscosity)) is less than 100, preferably less than 70, more preferably less than 50, still more preferably 1 to 30, and particularly preferably 1 to 5. The viscosity is measured with an E-type viscometer at a temperature of 25° C. and a rotational speed of 50 rpm, usually at atmospheric pressure.

The initial viscosity before the above standing of the polymerizable composition of the present invention is not particularly limited. For example, in an embodiment, the initial viscosity is 0.1 to 100,000 mPa·s, and preferably 0.1 to 20,000 mPa·s. The viscosity is measured with an E-type viscometer at a temperature of 25° C. and a rotational speed of 50 rpm, usually at atmospheric pressure.

[Polymerization Initiators]

A composition which does not include the acidic group-free polymerizable monomer (B) in the polymerizable composition of the present invention has an excellent performance as a polymerization initiator which exhibits superior storage stability and shows sufficiently high polymerization initiating activity upon addition of, for example, an acidic group-containing compound or a decomplexer.

That is, a composition which does not include the acidic group-free polymerizable monomer (B) in the polymerizable composition of the present invention is a polymerization initiator having outstanding storage stability and polymerization initiation performance. Such a composition which further contains a polymerization inhibitor attains still enhanced storage stability when the acidic group-free polymerizable monomer (B) is mixed therewith. The polymerization initiator exhibits excellent polymerization initiation performance by being used together with an acidic group-containing polymerizable monomer or a decomplexer.

Specifically, the polymerization initiator of the present invention includes the organoborane (A) and the stabilizer (C2) other than the Lewis bases (C1), and preferably further includes the Lewis base (C1). The details of the components of the polymerization initiator are the same as described in the section of [Polymerizable compositions], and the molar ratios such as the ratio of the organoborane (A) to the stabilizer (C) may be similar to those described in the section of [Polymerizable compositions].

Examples of the polymerization inhibitors include quinone compounds, phenol compounds having two or more substituents on the aromatic ring, catechol compounds, oxydiphenylamine compounds, nitroso compounds, nitrone compounds, nitrile compounds, hydrazyl compounds and phenothiazine compounds.

Some preferred quinone compounds are hydroquinone monomethyl ether, p-benzoquinone, 2,6-dichloro-p-benzoquinone, 2,5-dichloro-p-benzoquinone, 2-t-butylhydroquinone and butylhydroxyanisole.

A preferred phenol compound having two or more substituents on the aromatic ring is 3,5-t-dibutyl-6-hydroxytoluene.

Some preferred catechol compounds are catechol and 4-t-butylcatechol.

Some preferred oxydiphenylamine compounds are 2-oxydiphenylamine, isomers thereof which have the hydroxyl group at different positions (3-oxy isomer, 4-oxy isomer), and these amines described above which further have one or more substituents, for example, hydrocarbon groups such as methyl groups, and halogen atoms such as chlorine atoms.

Some preferred nitroso compounds are compounds which have a nitroso group bonded to an α carbon to the carbonyl such as methyl-α-nitrosoisopropyl ketone, and N-nitroso-N-phenylhydroxylamines such as N-nitroso-N-phenylhydroxylamine ammonium salt and N-nitroso-N-phenylhydroxylamine aluminum salt.

A preferred nitrone compound is phenyl-t-butylnitrone.

Some preferred nitrile compounds are compounds in which a nitrile group constitutes a conjugated system such as furfurylidenemalononitrile.

A preferred hydrazyl compound is 1,1-diphenyl-2-picrylhydrazyl.

Some preferred phenothiazine compounds are phenothiazine and derivatives thereof which have one or more substituents, for example, hydrocarbon groups such as methyl groups and halogen atoms such as chlorine atoms on the aromatic ring.

In the polymerization initiator, for example, the content of the polymerization inhibitor is usually 0.1 to 1000 parts by mass, and preferably 1 to 500 parts by mass with respect to 100 parts by mass of the component (A).

[Polymerizable Composition Kits]

The polymerizable composition kit of the present invention includes the aforementioned polymerizable composition of the invention (hereinafter, also written as the "composition (1)") containing the components (A) to (C), and an additive (hereinafter, also written as the "additive (2)") including a specific component. For example, the kit is stored as the individual composition (1) and additive (2) in separate containers. The polymerization curing takes place immediately, for example, within 1 hour, after mixing of the polymerizable composition (1) with the additive (2).

<Composition (1)>

The composition (1) is the polymerizable composition of the present invention described hereinabove.

<Additive (2)>

For example, the additive (2) is an acidic group-containing compound (α), or a composition including the compound (α). Alternatively, the additive (2) is a decomplexer (β) which shows reactivity with respect to the Lewis base (C1) so as to liberate the polymerization initiator component (A), or a composition including the decomplexer (β).

When the compound (α) or the decomplexer (β) is added to the aforementioned polymerizable composition of the invention, for example, the organoborane as a polymerization initiator is liberated from the organoborane-Lewis base complex and immediately initiates the polymerization of the polymerizable monomer to afford a cured product.

The above composition which includes the compound (α) or the decomplexer (β) may further contain at least one selected from the aforementioned components (B), (D) and (E) and the additional components (F). In a preferred embodiment, the composition further contains an acidic group-free polymerizable monomer (B).

<Acidic group-containing polymerizable compounds (α)>

Examples of the acidic groups in the compounds (α) include carboxylic acid groups such as carboxyl group and carboxylic anhydride group, phosphoric acid group, thiophosphoric acid group, pyrophosphoric acid group, sulfonic acid group and phosphonic acid group. The compound (α) may have a single, or two or more kinds of acidic groups.

Examples of the compounds (α) include polymerizable monomers having an acidic group.

Examples of the polymerizable monomers having a carboxyl group or an equivalent functional group (such as carboxylic anhydride group) include monocarboxylic acids, dicarboxylic acids, tricarboxylic acids, tetracarboxylic acids, polycarboxylic acids, and anhydrides of these acids.

Specific examples include monomers having a direct vinyl-carboxyl bond such as (meth)acrylic acid, fumaric acid and maleic acid; monomers having a group such as an aromatic ring between a vinyl group and a carboxyl group, such as p-vinylbenzoic acid; aliphatic carboxylic acids having a (meth)acryloyloxy group and one or more carboxyl groups, and anhydrides thereof, such as 11-(meth)acryloyloxy-1,1-undecanedicarboxylic acid (MAC-10 in the case of methacrylate); monocyclic aromatic carboxylic acids which have a linear hydrocarbon group containing one or more (meth)acryloyloxy groups and which have one or more carboxyl groups, and anhydrides thereof, such as 4-(meth)acryloyloxymethyltrimellitic acid, 4-(meth)acryloyloxyethyltrimellitic acid (4-MET in the case of methacrylate, 4-META in the case of the anhydride of methacrylate), 4-(meth)acryloyloxybutyltrimellitic acid, 1,4-di(meth)acryloyloxyethylpyromellitic acid, and 4-[2-hydroxy-3-(meth)acryloyloxy]butyltrimellitic acid; polycyclic aromatic carboxylic acids which have a linear hydrocarbon group containing one or more (meth)acryloyloxy groups and which have one or more carboxyl groups, and anhydrides thereof, such as 6-(meth)acryloyloxyethylnaphthalene-1,2,6-tricarboxylic acid; monocyclic aromatic carboxylic acids which have a linear hydrocarbon group containing one or more (meth)acryloyloxy groups and one or more hydrophilic functional groups such as hydroxyl groups and which have one or more carboxyl groups, and anhydrides thereof, such as 4-[2-hydroxy-3-(meth)acryloyloxy]butyltrimellitic acid; (meth)acrylates of alcohols which have one or more benzoyloxy groups containing one or more carboxyl groups, such as 2,3-bis(3,4-dicarboxybenzoyloxy)propyl (meth)acrylate; benzoic acids having one or more (meth)acryloyloxy groups, such as 2, 3 or 4-(meth)acryloyloxybenzoic acid; amino acids having an N-(meth)acryloyl group and/or an O-(meth)acryloyloxy group, such as O-(meth)acryloyloxy-N-(meth)acryloyltyrosine, O-(meth)acryloyloxytyrosine, N-(meth)acryloyltyrosine and N-(meth)acryloyloxyphenylalanine; N- and/or O-mono or di(meth)acryloylaminobenzoic acids such as N-(meth)acryloyl-p-aminobenzoic acid, N-(meth)acryloyl-O-aminobenzoic acid, N-(meth)acryloyl-5-aminosalicylic acid (5-MASA in the case of methacrylate) and N-(meth)acryloyl-4-aminosalicylic acid, adducts of N-phenylglycine or N-tolylglycine with glycidyl (meth)acrylate, and aminophthalic acids in which a linear hydrocarbon group containing a hydrophilic group such as a hydroxyl group and a (meth)acryloyloxy group is bonded to an amino group and/or a carboxyl group, such as 4-[(2-hydroxy-3-(meth)acryloyloxypropyl)amino] phthalic acid and 3 or 4-[N-methyl-N-(2-hydroxy-3-(meth) acryloyloxypropyl)amino]p hthalic acid. Of these, at least one selected from 11-methacryloyloxy-1,1-undecanedicarboxylic acid (MAC-10), 4-methacryloyloxyethyltrimellitic acid (4-MET), 4-MET anhydride (4-META) and N-methacryloyl-5-aminosalicylic acid (5-MASA) is preferable.

Examples of the polymerizable monomers having a phosphoric acid group or a thiophosphoric acid group include alkyl acid phosphates having one or more (meth)acryloyloxy groups, such as 2-(meth)acryloyloxyethyl acid phosphate, 2- and/or 3-(meth)acryloyloxypropyl acid phosphate, 4-(meth) acryloyloxybutyl acid phosphate, 6-(meth)acryloyloxyhexyl acid phosphate, 8-(meth)acryloyloxyoctyl acid phosphate, 10-(meth)acryloyloxydecyl acid phosphate and 12-(meth) acryloyloxydodecyl acid phosphate; and aromatic acid phosphates which have an alkyl group containing one or more (meth)acryloyloxy groups and which have 0 or more other substituents, such as 2-(meth)acryloyloxyethylphenyl acid phosphate and 2-(meth)acryloyloxyethyl-p-methoxyphenyl acid phosphate. The phosphoric acid groups in these compounds may be replaced by thiophosphoric acid groups. Of the above compounds, at least one selected from 2-methacryloyloxyethylphenyl acid phosphate (Phenyl P) and 10-methacryloyloxydecyl acid phosphate (MDP) is preferable.

Examples of the polymerizable monomers having a pyrophosphoric acid group include di{(meth)acryloyloxyalkyl} pyrophosphate compounds such as di{2-(meth)acryloyloxyethyl} pyrophosphate, di{4-(meth)acryloyloxybutyl} pyrophosphate, di{6-(meth)acryloyloxyhexyl} pyrophosphate, di{8-(meth)acryloyloxyoctyl} pyrophosphate and di{10-(meth)acryloyloxydecyl} pyrophosphate.

Examples of the polymerizable monomers having a sulfonic acid group include alkyl (meth)acrylates having one or more sulfonic acid groups and 0 or more other substituents (e.g., alkyls, halogens, alkoxies), such as 2-sulfoethyl (meth) acrylate, 2- or 1-sulfo-1- or -2-propyl (meth)acrylate, 1- or 3-sulfo-2-butyl (meth)acrylate, 3-bromo-2-sulfo-2-propyl (meth)acrylate and 3-methoxy-1-sulfo-2-propyl (meth)acrylate; and alkyl (meth)acrylamides having one or more sulfonic acid groups and 0 or more other substituents (e.g., alkyls, halogens, alkoxies), such as 1,1-dimethyl-2-sulfoethyl (meth)acrylamide. Of these, 2-methyl-2-(meth)acrylamidopropanesulfonic acid is preferable.

Examples of the polymerizable monomers having a phosphonic acid group include
3-(meth)acryloxypropyl-3-phosphonopropionate,
3-(meth)acryloxypropyl phosphonoacetate,
4-(meth)acryloxybutyl-3-phosphonopropionate,
4-(meth)acryloxybutyl phosphonoacetate,
5-(meth)acryloxypentyl-3-phosphonopropionate,
5-(meth)acryloxypentyl phosphonoacetate,
6-(meth)acryloxyhexyl-3-phosphonopropionate,
6-(meth)acryloxyhexyl phosphonoacetate,
10-(meth)acryloxydecyl-3-phosphonopropionate,
10-(meth)acryloxydecyl phosphonoacetate,
2-(meth)acryloxyethyl-phenyl phosphonate,
2-(meth)acryloyloxyethylphosphonic acid,
10-(meth)acryloyloxydecylphosphonic acid and
N-(meth)acryloyl-ω-aminopropylphosphonic acid.

The roles of the compound (α) are to liberate the organoborane from the organoborane-Lewis base complex to thereby cause the organoborane to initiate radical polymerization, and also to facilitate the permeation of the monomer (B) into hard tissues and to enhance its polymerizability. The compound (α) is more preferably at least one selected from 4-MET, 4-META, Phenyl P and MDP, and is particularly preferably at least one selected from 4-MET, 4-META and MDP.

The compounds (α) may be used singly, or two or more may be used in combination.

In the polymerizable composition kit of the present invention, the amount of the compound (α) in the additive (2) is usually 0.01 to 500 parts by mass, preferably 0.1 to 200 parts by mass, and more preferably 1 to 100 parts by mass with respect to 100 parts by mass of the total of the organoborane (A) and the acidic group-free polymerizable monomer (B) in the composition (1). This embodiment advantageously ensures that the organoborane will initiate the polymerization of the polymerizable monomer in a favorable manner.

<Decomplexers (β)>

An example of the decomplexers (β) is an amine-reactive compound which reacts with an amine so as to separate the chemical bond between the amine and the organoborane and thereby to liberate the organoborane from the organoborane-amine complex. The same applies to the Lewis bases (C1) other than amines.

The amine-reactive compound is preferably such a substance that can easily form a reaction product with an amine at about room temperature, for example, about 20 to 22° C. Such a compound is advantageous in that the composition can be generally used and cured with ease under ambient conditions.

Examples of the decomplexers (β) include acids, aldehydes, isocyanates, acid chlorides, sulfonyl chlorides, and mixtures of two or more of these compounds. Acids are preferable. Both Bronsted acids and Lewis acids may be used. U.S. Pat. No. 5,718,977 to Pocius, 9th column, lines 1-15, describes preferred acid compounds (such compounds disclosed are incorporated herein by reference). The most preferred acid is (meth)acrylic acid. Examples further include the aforementioned polymerizable monomers having an acidic group.

In the polymerizable composition kit of the present invention, the amount of the decomplexer (β) in the additive (2) is usually 0.01 to 500 parts by mass, preferably 0.1 to 200 parts by mass, and more preferably 1 to 100 parts by mass with respect to 100 parts by mass of the total of the organoborane (A) and the acidic group-free polymerizable monomer (B) in the composition (1). This embodiment advantageously ensures that the organoborane-amine complex will be dissociated sufficiently and the resultant organoborane will initiate the polymerization of the polymerizable monomer in a favorable manner.

<Configurations of Polymerizable Composition Kits of Invention>

In the polymerizable composition kit of the present invention, the lower limit of the amount of the polymerizable monomer(s) is preferably 10 mass %, and more preferably 30 mass % based on the total mass of the composition obtained by mixing the polymerizable composition (1) and the additive (2), and the upper limit on the same basis is preferably 95 mass %, more preferably 90 mass %, and still more preferably 85 mass %. For example, the polymerizable monomers include an acidic group-free polymerizable monomer (B) and a polymerizable monomer having an acidic group.

In the polymerizable composition kit of the present invention, the lower limit of the amount of the organoborane-Lewis base complex is preferably 0.01 mass %, more preferably 0.1 mass %, and still more preferably 1 mass % based on the total mass of the composition obtained by mixing the polymerizable composition (1) and the additive (2), and the upper limit on the same basis is preferably 30 mass %, more preferably 20 mass %, and still more preferably 10 mass %.

When the polymerizable composition kit of the present invention involves the polymer (D) and/or the filler (E), the amount of the polymer (D) is, for example, 1 to 300 parts by mass and the amount of the filler (E) is, for example, 0.1 to 500 parts by mass with respect to 100 parts by mass of the total of the components (A) and (B) in the polymerizable composition (1) and the additive (2).

[Use Applications of Polymerizable Compositions and Kits]

The polymerizable compositions and the kits of the present invention may be suitably used as adhesives and as coating agents, and also may be suitably used in medical and/or dental applications. They may be particularly suitably used as adhesives and coating agents in the above applications.

For example, the polymerizable compositions and the kits of the present invention are suited as adhesives and coating agents in the applications described above, and are particularly suited as adhesives for the bonding of biological hard tissues to one another, adhesives for the bonding between an adherend and a hard tissue, and coating agents for the surface of an adherend or a hard tissue. Examples of the biological hard tissues include tooth structures and bones. Examples of the adherends include dental metals, dental alloys, dental porcelains and dental resins.

Because the polymerizable composition of the present invention has excellent adhesion with respect to biological hard tissues and attains high adhesion even when the hard tissues have been pretreated and also from the point of view of the mechanism in which polymerization is initiated, the composition is preferably used in combination with pretreatment. Although performing a pretreatment on hard tissues does not provide any particular effects in the initial adhesion attained by the polymerizable composition kit of the present invention, it is preferable from the point of view of adhesion durability that the kit be used in combination with pretreatment. Examples of the pretreatments include etching with a tooth surface-treating agent containing an acid, and surface modification with a tooth surface-treating agent containing an oxidizer.

In detail, when the polymerizable composition or the kit of the present invention is used in direct contact with tooth structure, the surface of the tooth structure is pretreated in accordance with the situation and the polymerizable composition or the kit of the invention is thereafter applied. In this manner, adhesion durability is advantageously enhanced.

The pretreatment may involve a pretreatment agent containing an acid such as a Lewis acid. Some example agents are aqueous solutions with 5 or less pH which contain, for example, an acid free from ethylenically unsaturated double bonds such as hydrochloric acid, nitric acid, sulfuric acid, phosphoric acid, citric acid or oxalic acid, or an acidic group-containing polymerizable monomer such as maleic acid, 4-META or MDP and which optionally further contain an organic solvent; and aqueous solutions which contain a chelating compound such as ethylenediamine tetraacetate (EDTA). Examples of the pretreatment agents further include hydrogen peroxide solution and aqueous sodium hypochlorite solution. From the point of view of polymerization initiation, the polymerizable composition of the present invention is preferably used in combination with pH 5 or less aqueous solution or with hydrogen peroxide or aqueous sodium hypochlorite solution.

EXAMPLES

The present invention will be described in further detail based on EXAMPLES. However, it should be construed that the scope of the present invention is not limited to such EXAMPLES.

Synthesis of Organoborane-Lewis Base Complexes

Synthetic Example 1

A flask was purged with nitrogen and was loaded with 0.1 mol of 1,3-diaminopropane. A solution of 0.1 mol of triethylborane in 100 mL of tetrahydrofuran was added to the flask. After the whole of the triethylborane solution had been added, stirring was performed for about 1 hour while performing cooling to keep the solution in the flask at about 40° C. Thereafter, the tetrahydrofuran was removed with a rotary evaporator. Triethylborane-1,3-diaminopropane complex (TEB-DAP) was thus obtained.

Synthetic Example 2

Tributylborane-3-methoxy-1-propylamine complex (TBB-MPA) was obtained in the same manner as in SYNTHETIC EXAMPLE 1, except that 1,3-diaminopropane was replaced by 3-methoxy-1-propylamine and triethylborane was replaced by tri-n-butylborane.

Synthetic Example 3

Triethylborane-diethylenetriamine complex (TEB-DETA) was obtained in the same manner as in SYNTHETIC EXAMPLE 1, except that 1,3-diaminopropane was replaced by diethylenetriamine.

Preparation of Polymerizable Compositions

Example 1

A polymerizable composition was obtained by mixing 0.21 g of TEB-DAP obtained in SYNTHETIC EXAMPLE 1 with 5.0 g of methyl methacrylate (MMA) and 0.07 g of ascorbic acid.

Examples 2 to 14 and Comparative Examples 1 to 5

Polymerizable compositions were obtained in the same manner as in EXAMPLE 1, except that the formulation in EXAMPLE 1 was changed as described in Table 1-1 and Table 1-2 (also collectively referred to as "Table 1"). When the complexes described above were used, the amounts of (A) and (C1) in Table 1 are the amounts of the components constituting the complex.

Example 15

Part A of polymerizable composition kit was prepared by mixing 0.21 g of TEB-DAP obtained in SYNTHETIC EXAMPLE 1 with 2.5 g of MMA and 0.07 g of ascorbic acid. Next, Part B of polymerizable composition kit was prepared by mixing 2.5 g of MMA with 0.25 g of 4-methacryloyloxyethyltrimellitic anhydride (4-META) and 9.5 g of polymethyl methacrylate (PMMA). The PMMA had a weight average molecular weight of 400,000 as measured by gel permeation chromatography relative to polymethyl methacrylate standards, and a volumetric average particle size of 32 μm as measured with a grain size distribution analyzer (laser diffraction/scattering method). Part A and Part B were stored separately, and were mixed together at the time of use.

Examples 16 to 21

Polymerizable composition kits were obtained in the same manner as in EXAMPLE 15, except that the formulations in EXAMPLE 15 were changed as described in Table 2. The amounts of (A) and (C1) in Table 2 are the amounts of the components constituting the complex. "TMPT.f" is a filler obtained by polymerizing polymerizable monomers based on trimethylolpropane tri(meth)acrylate (TMPT) so as to coat fine powdery silica, and crushing the resultant polymer.

<<Evaluations>>

<Thermal Stability Test>

The polymerizable compositions obtained in EXAMPLES and COMPARATIVE EXAMPLES were added to glass sample bottles. The filled bottles were allowed to stand in an oven set at 45° C. The degree of polymerization was examined visually and by touch 1 hour, 15 hours, 48 hours, 96 hours and 168 hours after the start of standing. Evaluation was made based on the ratio of viscosities before and after the standing according to the criteria described below. The results are shown in Table 1 or Table 2. In EXAMPLES 15 to 21, Part A of the polymerizable composition kit was used alone without being mixed with Part B. The viscosity was measured with an E-type viscometer at 25° C., 50 rpm and atmospheric pressure.

When the composition remained as liquid: AA (The viscosity ratio was 1 to 5.)
When the composition had increased its viscosity: BB (The viscosity ratio was more than 5 to less than 100.)
When the composition had been cured: CC (The viscosity ratio was 100 or above.)

<Long-Term Stability Test>

The polymerizable compositions obtained in EXAMPLES and COMPARATIVE EXAMPLES were added to glass sample bottles. The filled bottles were allowed to stand at room temperature (25° C.). The degree of polymerization was examined visually and by touch 3 days, 7 days, 3 months, 6 months and 12 months after the start of standing. Evaluation was made based on the ratio of viscosities before and after the standing according to the criteria described below. The results are shown in Table 1 or Table 2. In EXAMPLES 15 to 21, Part A of the polymerizable composition was used alone without being mixed with Part B.

The viscosity was measured with an E-type viscometer at 25° C., 50 rpm and atmospheric pressure.

When the composition remained as liquid: AA (The viscosity ratio was 1 to 5.)
When the composition had increased its viscosity: BB (The viscosity ratio was more than 5 to less than 100.)
When the composition had been cured: CC (The viscosity ratio was 100 or above.)

<Adhesion Test>

Fresh bovine mandibular anterior teeth that had been frozen after removal were thawed. With use of rotational polishing machine ECOMET-III (BUEHLER), the anterior teeth were polished with waterproof emery paper #180 while pouring water and applying finger pressure so as to expose a flat face of enamel or dentin.

The water sitting on the polished tooth surface was removed by air blowing. Immediately thereafter, the tooth was fixed to a 1 mm thick mold which had a pressure-sensitive adhesive spread on one side and had a circular hole 4.8 mm in inner diameter, so that the polished tooth surface was directed upward. Next, a teeth primer containing 4-META (Sun Medical Co., Ltd.) was applied to the flat face of enamel or dentin, and was allowed to stand for 20 seconds. Thereafter, the solvent component present in the primer was removed by air blowing. Adherends were thus obtained.

The polymerizable compositions from EXAMPLES 1 to 14, which had been allowed to stand at 45° C. for 168 hours in the thermal stability test, were applied to the surface of the adherends. After air blowing, acrylic rods were placed upright thereon. Parts A of the polymerizable compositions from EXAMPLES 15 to 21 after the thermal stability test were mixed with Parts B, and the resultant polymerizable compositions were applied to the surface of the adherends, and acrylic rods were placed upright thereon. Those polymerizable compositions which had been evaluated as CC under the aforementioned conditions were not tested for adhesion. Further, the polymerizable compositions from COMPARATIVE EXAMPLES 1 to 5, immediately after their preparation, were applied to the surface of the adherends, air was blown thereto, and acrylic rods were placed upright.

After the acrylic rods were placed upright, the units were allowed to stand for 1 hour and were immersed in water at 37° C. overnight. The tensile strength was measured at a crosshead speed of 2 mm/min. The results are described in Table 1 and Table 2.

The results in Table 1 and Table 2 show that the polymerizable compositions of the present invention have superior thermal stability and long-term stability, and also exhibit outstanding adhesion with respect to tooth structures that are hard tissues. Thus, the polymerizable compositions of the present invention are particularly effective as medical and/or dental materials.

TABLE 1

| | | | | Comp. Ex. 1 | Comp. Ex. 2 | Comp. Ex. 3 | Comp. Ex. 4 | Comp. Ex. 5 |
|---|---|---|---|---|---|---|---|---|
| Polymerizable compositions | Organoboranes (A) | | Tri-n-butylborane | | 0.22 | 0.22 | | 0.22 |
| | | | Triethylborane | 0.12 | | | 0.12 | |
| | Polymerizable monomers (B) | | Methyl methacrylate | 5.0 | 5.0 | 5.0 | 5.0 | |
| | | | 2,2-Bis(4-methacryloxypolyethoxy-phenyl)propane*1 | | | | | 5.0 |
| | Stabilizers (C) | (C1) | 1,3-Diaminopropane | | | | 0.09 | |
| | | | 3-Methoxy-1-propylamine | | | 0.11 | | 0.11 |
| | | | Diethylenetriamine | | | | | |
| | | (C2) | C2b: ascorbic acid | | | | | |

TABLE 1-continued

|  |  |  |  |  |  |  |  |  |
|---|---|---|---|---|---|---|---|---|
|  |  |  | C2b: α-tocopherol |  |  |  |  |  |
|  |  |  | C2a: 1-phenyl-1,2-propanedione |  |  |  |  |  |
|  |  |  | C2a: acetylacetone |  |  |  |  |  |
|  |  |  | C2a: 2,5-hexanedione |  |  |  |  |  |
|  |  |  | C2a: 2,3-butanedione |  |  |  |  |  |
|  |  |  | C2b: calciferol |  |  |  |  |  |
|  |  |  | C2b: quercetin |  |  |  |  |  |
|  |  |  | C2c: β-carotene |  |  |  |  |  |
|  |  |  | C2d: dibutyltin dilaurate |  |  |  |  |  |
|  |  |  | C2d: magnesium aluminometasilicate |  |  |  |  |  |
| Evaluations | Thermal stability test 45° C. |  | Viscosity ratio (viscosity after 48 hours of standing at 45° C./initial viscosity) | >100 | >100 | >100 | >100 | >100 |
|  |  |  | 1 hour | CC | CC | AA | AA | AA |
|  |  |  | 15 hours | — | — | CC | BB | CC |
|  |  |  | 48 hours |  |  |  | CC |  |
|  |  |  | 96 hours | — | — | — | — | — |
|  |  |  | 168 hours | — | — | — | — | — |
|  | Long-term stability test 25° C. |  | 3 days | CC | CC | CC | AA | CC |
|  |  |  | 7 days | — | — | — | BB | — |
|  |  |  | 3 months | — | — | — | CC | — |
|  |  |  | 6 months | — | — | — | — | — |
|  |  |  | 12 months | — | — | — | — | — |
|  | Adhesion test (MPa) |  | Enamel | 6.8 | 7.2 | 7.4 | 6.2 | 6.3 |
|  |  |  | Dentin | 6.9 | 6.9 | 6.4 | 7.1 | 6.1 |

|  |  |  |  | Ex. 1 | Ex. 2 | Ex. 3 | Ex. 4 | Ex. 5 |
|---|---|---|---|---|---|---|---|---|
| Polymerizable compositions | Organoboranes (A) |  | Tri-n-butylborane |  | 0.22 |  | 0.22 | 0.22 |
|  |  |  | Triethylborane | 0.12 |  | 0.12 |  |  |
|  | Polymerizable monomers (B) |  | Methyl methacrylate | 5.0 | 5.0 | 5.0 | 5.0 | 5.0 |
|  |  |  | 2,2-Bis(4-methacryloxypolyethoxy-phenyl)propane*1 |  |  |  |  |  |
|  | Stabilizers (C) | (C1) | 1,3-Diaminopropane | 0.09 |  |  |  |  |
|  |  |  | 3-Methoxy-1-propylamine |  | 0.11 |  | 0.11 | 0.11 |
|  |  |  | Diethylenetriamine |  |  | 0.12 |  |  |
|  |  | (C2) | C2b: ascorbic acid | 0.07 | 0.07 |  |  |  |
|  |  |  | C2b: α-tocopherol |  |  | 0.17 | 0.17 |  |
|  |  |  | C2a: 1-phenyl-1,2-propanedione |  |  |  |  | 0.06 |
|  |  |  | C2a: acetylacetone |  |  |  |  |  |
|  |  |  | C2a: 2,5-hexanedione |  |  |  |  |  |
|  |  |  | C2a: 2,3-butanedione |  |  |  |  |  |
|  |  |  | C2b: calciferol |  |  |  |  |  |
|  |  |  | C2b: quercetin |  |  |  |  |  |
|  |  |  | C2c: β-carotene |  |  |  |  |  |
|  |  |  | C2d: dibutyltin dilaurate |  |  |  |  |  |
|  |  |  | C2d: magnesium aluminometasilicate |  |  |  |  |  |
| Evaluations | Thermal stability test 45° C. |  | Viscosity ratio (viscosity after 48 hours of standing at 45° C./initial viscosity) | 1 | 1 | 1 | 1 | 1 |
|  |  |  | 1 hour | AA | AA | AA | AA | AA |
|  |  |  | 15 hours | AA | AA | AA | AA | AA |
|  |  |  | 48 hours | AA | AA | AA | AA | AA |
|  |  |  | 96 hours | AA | BB | AA | AA | AA |
|  |  |  | 168 hours | BB | BB | AA | AA | AA |
|  | Long-term stability test 25° C. |  | 3 days | AA | AA | AA | AA | AA |
|  |  |  | 7 days | AA | AA | AA | AA | AA |
|  |  |  | 3 months | AA | AA | AA | AA | AA |
|  |  |  | 6 months | AA | AA | AA | AA | AA |
|  |  |  | 12 months | BB | BB | AA | AA | AA |
|  | Adhesion test (MPa) |  | Enamel | 4.6 | 5.1 | 6.1 | 6.6 | 7.8 |
|  |  |  | Dentin | 4.8 | 4.2 | 6.9 | 7.2 | 7.9 |

|  |  |  |  | Ex. 6 | Ex. 7 | Ex. 8 | Ex. 9 | Ex. 10 | Ex. 11 |
|---|---|---|---|---|---|---|---|---|---|
| Polymerizable compositions | Organoboranes (A) |  | Tri-n-butylborane | 0.22 | 0.22 | 0.22 | 0.22 | 0.22 | 0.22 |
|  |  |  | Triethylborane |  |  |  |  |  |  |
|  | Polymerizable monomers (B) |  | Methyl methacrylate | 5.0 | 5.0 | 5.0 | 5.0 | 5.0 | 5.0 |
|  |  |  | 2,2-Bis(4-methacryloxypolyethoxy-phenyl)propane*1 |  |  |  |  |  |  |
|  | Stabilizers (C) | (C1) | 1,3-Diaminopropane |  |  |  |  |  |  |
|  |  |  | 3-Methoxy-1-propylamine | 0.11 | 0.11 | 0.11 | 0.11 | 0.11 | 0.11 |
|  |  |  | Diethylenetriamine |  |  |  |  |  |  |
|  |  | (C2) | C2b: ascorbic acid |  |  |  |  |  |  |
|  |  |  | C2b: α-tocopherol |  |  |  |  |  |  |
|  |  |  | C2a: 1-phenyl-1,2-propanedione | 0.04 |  |  |  |  |  |
|  |  |  | C2a: acetylacetone |  | 0.05 |  |  |  |  |
|  |  |  | C2a: 2,5-hexanedione |  |  | 0.03 |  |  |  |
|  |  |  | C2a: 2,3-butanedione |  |  |  |  |  |  |
|  |  |  | C2b: calciferol |  |  |  | 0.16 |  |  |
|  |  |  | C2b: quercetin |  |  |  |  | 0.12 |  |
|  |  |  | C2c: β-carotene |  |  |  |  |  | 0.21 |

TABLE 1-continued

| | | | | | | | | | |
|---|---|---|---|---|---|---|---|---|---|
| Evaluations | Thermal stability test 45° C. | C2d: dibutyltin dilaurate C2d: magnesium aluminometasilicate Viscosity ratio (viscosity after 48 hours of standing at 45° C./initial viscosity) | | 15 | 6 | 1 | 1 | 7 | 1 |
| | | 1 hour | | AA | AA | AA | AA | AA | AA |
| | | 15 hours | | AA | AA | AA | AA | AA | AA |
| | | 48 hours | | BB | BB | AA | AA | BB | AA |
| | | 96 hours | | CC | BB | AA | AA | BB | AA |
| | | 168 hours | | — | CC | AA | AA | CC | AA |
| | Long-term stability test 25° C. | 3 days | | AA | AA | AA | AA | AA | AA |
| | | 7 days | | AA | AA | AA | AA | AA | AA |
| | | 3 months | | AA | AA | AA | AA | AA | AA |
| | | 6 months | | BB | AA | AA | AA | BB | AA |
| | | 12 months | | CC | BB | AA | AA | BB | AA |
| | Adhesion test (MPa) | Enamel | | — | — | 6.5 | 6.2 | — | 5.4 |
| | | Dentin | | — | — | 6.6 | 7.4 | — | 4.2 |

| | | | | Ex. 12 | Ex. 13 | Ex. 14 |
|---|---|---|---|---|---|---|
| Polymerizable compositions | Organoboranes (A) | | Tri-n-butylborane | 0.22 | 0.22 | 0.22 |
| | | | Triethylborane | | | |
| | Polymerizable monomers (B) | | Methyl methacrylate | 5.0 | 5.0 | |
| | | | 2,2-Bis(4-methacryloxypolyethoxy-phenyl)propane*1 | | | 5.0 |
| | Stabilizers (C) | (C1) | 1,3-Diaminopropane | | | |
| | | | 3-Methoxy-1-propylamine | 0.11 | 0.11 | 0.11 |
| | | | Diethylenetriamine | | | |
| | | (C2) | C2b: ascorbic acid | | | |
| | | | C2b: α-tocopherol | | | |
| | | | C2a: 1-phenyl-1,2-propanedione | | | 0.06 |
| | | | C2a: acetylacetone | | | |
| | | | C2a: 2,5-hexanedione | | | |
| | | | C2a: 2,3-butanedione | | | |
| | | | C2b: calciferol | | | |
| | | | C2b: quercetin | | | |
| | | | C2c: β-carotene | | | |
| | | | C2d: dibutyltin dilaurate | 0.25 | | |
| | | | C2d: magnesium aluminometasilicate | | 0.30 | |
| Evaluations | Thermal stability test 45° C. | | Viscosity ratio (viscosity after 48 hours of standing at 45° C./initial viscosity) | 1 | 15 | 12 |
| | | | 1 hour | AA | AA | AA |
| | | | 15 hours | AA | AA | AA |
| | | | 48 hours | AA | BB | BB |
| | | | 96 hours | AA | CC | BB |
| | | | 168 hours | AA | — | CC |
| | Long-term stability test 25° C. | | 3 days | AA | AA | AA |
| | | | 7 days | AA | AA | AA |
| | | | 3 months | AA | AA | AA |
| | | | 6 months | AA | BB | BB |
| | | | 12 months | AA | CC | CC |
| | Adhesion test (MPa) | | Enamel | 5.5 | — | — |
| | | | Dentin | 4.8 | — | — |

*The unit of the values for components in the polymerizable compositions is g.
*1BPE-100 (Shin-Nakamura Chemical Co., Ltd.)

TABLE 2

| | | | | | Ex. 15 | Ex. 16 | Ex. 17 | Ex. 18 |
|---|---|---|---|---|---|---|---|---|
| Polymerizable composition kits | Part A | Organoboranes (A) | | Tri-n-butylborane | | | 0.22 | 0.22 |
| | | | | Triethylborane | 0.12 | 0.12 | | |
| | | Polymerizable monomers (B) | | Methyl methacrylate | 2.5 | 2.5 | 2.5 | 2.5 |
| | | | | 2,2-Bis(4-methacryloxypolyethoxy-phenyl)propane | | | | |
| | | Stabilizers (C) | (C1) | 1,3-Diaminopropane | 0.09 | | | |
| | | | | 3-Methoxy-1-propylamine | | | 0.11 | 0.11 |
| | | | | Diethylenetriamine | | 0.12 | | |
| | | | (C2) | C2b: ascorbic acid | 0.07 | 0.07 | | |
| | | | | C2b: α-tocopherol | | | 0.17 | |
| | | | | C2a: 1-phenyl-1,2-propanedione | | | | 0.06 |
| | Part B | Polymerizable monomer (B) | | Methyl methacrylate | 2.5 | 2.5 | 2.5 | 2.5 |
| | | Acidic group-containing compounds (α) | | 4-Methacryloyloxyethyltrimellitic anhydride | 0.25 | 0.25 | 0.25 | 0.25 |
| | | | | 4-Methacryloyloxyethyltrimellitic acid | | | | |
| | | | | 10-Methacryloyloxydecyl acid phosphate | | | | |
| | | Polymer (D) | | Polymethyl methacrylate | 9.5 | 9.5 | 8.5 | 9.5 |
| | | Filler (E) | | TMPT·f | | | 1.0 | |

TABLE 2-continued

| Evaluations | Part A | Thermal stability test 45° C. | Viscosity ratio (viscosity after 48 hours of standing at 45° C./initial viscosity) | 1 | 1 | 1 | 1 |
|---|---|---|---|---|---|---|---|
| | | | 1 hour | AA | AA | AA | AA |
| | | | 15 hours | AA | AA | AA | AA |
| | | | 48 hours | AA | AA | AA | AA |
| | | | 96 hours | AA | AA | AA | AA |
| | | | 168 hours | BB | AA | AA | AA |
| | | Long-term stability test 25° C. | 3 days | AA | AA | AA | AA |
| | | | 7 days | AA | AA | AA | AA |
| | | | 3 months | AA | AA | AA | AA |
| | | | 6 months | AA | AA | AA | AA |
| | | | 12 months | AA | AA | AA | AA |
| | Adhesion test (MPa) | | Enamel | 7.6 | 10.1 | 10.6 | 10.3 |
| | | | Dentin | 7.2 | 9.6 | 9.9 | 9.5 |

| | | | | Ex. 19 | Ex. 20 | Ex. 21 |
|---|---|---|---|---|---|---|
| Polymerizable composition kits | Part A | Organoboranes (A) | Tri-n-butylborane | 0.22 | 0.22 | |
| | | | Triethylborane | | | 0.12 |
| | | Polymerizable monomers (B) | Methyl methacrylate | 2.5 | 2.5 | 1.5 |
| | | | 2,2-Bis(4-methacryloxypolyethoxy-phenyl)propane | | | 1.0 |
| | | Stabilizers (C) (C1) | 1,3-Diaminopropane | | | 0.09 |
| | | | 3-Methoxy-1-propylamine | 0.11 | 0.11 | |
| | | | Diethylenetriamine | | | |
| | | (C2) | C2b: ascorbic acid | | | 0.07 |
| | | | C2b: α-tocopherol | 0.17 | | |
| | | | C2a: 1-phenyl-1,2-propanedione | | 0.06 | |
| | Part B | Polymerizable monomer (B) | Methyl methacrylate | 2.5 | 2.5 | 2.5 |
| | | Acidic group-containing compounds (α) | 4-Methacryloyloxyethyltrimellitic anhydride | | | 0.25 |
| | | | 4-Methacryloyloxyethyltrimellitic acid | 0.25 | | |
| | | | 10-Methacryloyloxydecyl acid phosphate | | 0.25 | |
| | | Polymer (D) | Polymethyl methacrylate | 9.5 | 9.5 | 9.5 |
| | | Filler (E) | TMPT · f | | | |
| Evaluations | Part A | Thermal stability test 45° C. | Viscosity ratio (viscosity after 48 hours of standing at 45° C./initial viscosity) | 1 | 1 | 1 |
| | | | 1 hour | AA | AA | AA |
| | | | 15 hours | AA | AA | AA |
| | | | 48 hours | AA | AA | AA |
| | | | 96 hours | AA | AA | AA |
| | | | 168 hours | AA | AA | BB |
| | | Long-term stability test 25° C. | 3 days | AA | AA | AA |
| | | | 7 days | AA | AA | AA |
| | | | 3 months | AA | AA | AA |
| | | | 6 months | AA | AA | AA |
| | | | 12 months | AA | AA | AA |
| | Adhesion test (MPa) | | Enamel | 11.0 | 11.5 | 6.6 |
| | | | Dentin | 10.8 | 10.6 | 6.1 |

*The unit of the values for components in the polymerizable composition kits is g.

The invention claimed is:

1. A polymerizable composition comprising
(A) an organoborane,
(B) an acidic group-free polymerizable monomer, and
(C) a stabilizer for the organoborane (A),
  wherein the stabilizer (C) includes
(C1) a Lewis bases capable of forming a complex with the organoborane (A), and
(C2) a stabilizer other than (C1),
  a molar ratio (C1/C2) of the Lewis base (C1) to the stabilizer (C2) is 0.1 to 20,
  the stabilizer (C2) is at least one selected from
(C2a) compounds which have a conjugated electron system, have a diketone structure, and have a hydrogen atom belonging to the conjugated electron system and not bonded directly to an aromatic ring,
(C2b) compounds which have a conjugated electron system constituting at least part of a ring structure, and have a hydrogen atom belonging to the conjugated electron system and not bonded directly to an aromatic ring,
(C2c) compounds which have a conjugated electron system containing five or more double bonds, and have a hydrogen atom belonging to the conjugated electron system and not bonded directly to an aromatic ring, and
(C2d) at least one class of compounds selected from reducing compounds, hydrotalcite-like compounds and metal salts.

2. The polymerizable composition described in claim 1, wherein the organoborane (A) is a compound represented by BR3 wherein R independently at each occurrence is a C1-20 alkyl group.

3. The polymerizable composition described in claim 1, which comprises an organoborane-Lewis base complex formed from the organoborane (A) and the Lewis base (C1).

4. The polymerizable composition described in claim 1, wherein the Lewis base (C1) is at least one selected from ammonia, amines, hydroxides and alkoxides.

5. The polymerizable composition described in claim 1, wherein the compound (C2a) is at least one selected from α-diketones and β-diketones.

6. The polymerizable composition described in claim 1, wherein the content of the stabilizer (C) is 0.001 to 100 parts by mass with respect to 100 parts by mass of the total of the components (A) and (B).

7. The polymerizable composition described in claim 1, which further comprises a polymer (D) that is swollen by the polymerizable monomer (B) or is dissolved into the polymerizable monomer (B).

8. The polymerizable composition described in claim 7, wherein the polymer (D) is a polymethyl (meth)acrylate.

9. The polymerizable composition described in claim 1, which further comprises a filler (E).

10. The polymerizable composition described in claim 9, wherein the content of the filler (E) is 0.1 to 500 parts by mass with respect to 100 parts by mass of the total of the components (A) and (B).

11. The polymerizable composition described in claim 1, which is used in combination with an acid-containing pretreatment agent.

12. The polymerizable composition described in claim 1, which is used as an adhesive.

13. The polymerizable composition described in claim 1, which is used in a medical and/or a dental application.

14. The polymerizable composition or the polymerizable composition kit described in claim 13, which is used as an adhesive in a medical and/or a dental application in combination with a tooth surface-treating agent including an acid or an oxidizer.

15. A polymerizable composition kit comprising the polymerizable composition described in claim 1, and an additive wherein the additive comprises an acidic group-containing compound (α) or a composition including the compound (α).

16. The polymerizable composition kit described in claim 15, wherein the acidic group-containing compound (α) is an acidic group-containing polymerizable monomer.

17. The polymerizable composition kit described in claim 16, wherein the acidic group-containing polymerizable monomer is at least one selected from 4-methacryloyloxyethyl trimellitic acid, 4-methacryloyloxyethyltrimellitic anhydride, and 10-methacryloyloxydecyl acid phosphate.

18. A polymerizable composition kit comprising the polymerizable composition described in claim 1, and an additive wherein the additive comprises a decomplexer (β) having reactivity with the Lewis base (C1) capable of forming a complex with the organoborane (A), or a composition including the decomplexer (β).

19. The polymerizable composition kit described in claim 18, wherein the decomplexer (β) is an acid, an aldehyde, an isocyanate, an acid chloride, a sulfonyl chloride, or a mixture of two or more of these compounds.

* * * * *